United States Patent [19]

Jacklich

[11] 4,362,511
[45] Dec. 7, 1982

[54] J BOLT

[76] Inventor: John Jacklich, 102 Western Ct., Santa Cruz, Calif. 95060

[21] Appl. No.: 281,574

[22] Filed: Jul. 9, 1981

[51] Int. Cl.³ .............................................. A61C 5/08
[52] U.S. Cl. .................................................. 433/220
[58] Field of Search ................ 433/177, 220, 169, 170

[56] References Cited

U.S. PATENT DOCUMENTS 2,691,219  10/1954  Sandri ................................ 433/177

FOREIGN PATENT DOCUMENTS 508020  1/1955  Italy ..................................... 433/170

Primary Examiner—Robert Peshock
Attorney, Agent, or Firm—Robert G. Slick

[57] ABSTRACT

A threaded device is provided which can be screwed into the tooth root of a broken tooth to aid in the attachment of a crown or similar prosthesis. The threaded device has a head which is in the shape of a spherical segment of less than a hemisphere which holds a retention ring, a shim, and in some embodiments a coping dish whereby the device of the present invention can be screwed into a threaded hole in the tooth, a dental cement applied thereto and a crown or other prosthesis applied over the head of the bolt and retention ring. In a preferred embodiment of the invention, the retention ring is in the form of a spherical segment which is complementary to the spherical segment of the head to provide a complete spherical head.

5 Claims, 8 Drawing Figures

J BOLT

SUMMARY OF THE INVENTION

Various anchoring devices have been proposed by which a tooth crown or the like can be attached to a broken off tooth.

Devices used in the past have not been fully satisfactory in that they require that after the broken tooth is prepared that an impression be taken of the tooth and then a cap cast of a metal such as gold, porcelain coated platinum or the like. This is a relatively expensive procedure and requires several visits to the dentist while the technique of the present invention permits one to prepare and fit a crown very quickly and even to use stock parts so that the whole operation can be completed in a single visit to the dentist.

Another deficiency with prior art devices is that they frequently are insecure and allow the retaining post to wobble so that the post has a tendency to come loose in the tooth root. In contrast, the device of the present invention is very securely attached to the tooth and is provided with a large retention ring so that a firm grip is secured over a large area of both the tooth stump and the prosthesis.

In accordance with one aspect of the present invention, a threaded device is provided with a head which is a spherical segment which is less than a hemisphere and wherein a retainer is employed which is complementary thereto and completes the sphere. In accordance with another embodiment of the invention, a retention ring is provided in the form of an oblate spheroid of metal which provides a large area and thus firm gripping of the prosthesis when a corresponding depression in the prosthesis is filled with silicone.

Other features and advantages of the invention will be brought out in the balance of the specification.

DESCRIPTION OF THE PREFERRED EMBODIMENT

Figure 1:
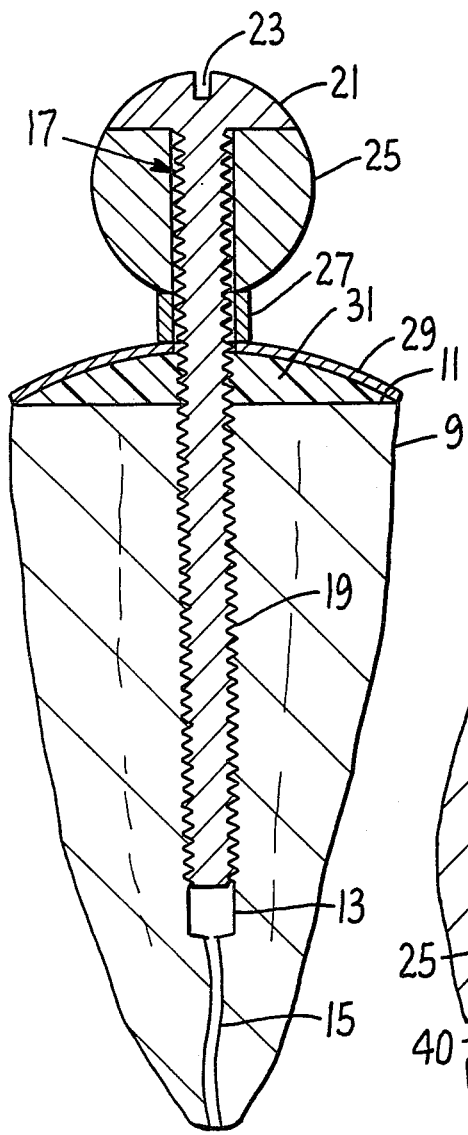
FIG. 1 is a section of a denture retaining device embodying the present invention.

The device and method of the present invention relate to the securing of a dental prosthesis crown or the like to the stump or root of a broken off tooth. In the embodiment of the invention shown in FIGS. 1-3 the broken off tooth is designated 9 and ideally it would have a flat top surface 11 although the flat surface is not essential to carrying out the present invention. In order to prepare the tooth a hole 13 is drilled into the top of the tooth following the root canal 15. The root canal would normally be filled with a material as is well known to those skilled in the art. The hole is then tapped for the reception of a screw hereafter described.

The device of the present invention includes a screw generally designated 17 having a threaded shaft 19 and a head 21. The head 21 is in the form of a spherical segment of less than half a hemisphere and is provided with the usual slot 23 for driving the screw. In this embodiment of the inventin a retainer 25 is employed which is also a spherical segment but which is more than a hemisphere and is complementary to the head 21 so that when the retainer 25 is placed against the head 21 a substantially complete sphere is provided. A shim 27 is provided and a coping dish 29. The coping dish 29 has a central opening 31 so that the shaft 19 can easily pass through the dish.

In order to utilize the present invention, the tooth 9 which has been drilled and tapped as described previously, is covered on the top surface 11 with a dental composite 31. The coping dish 29 is then placed over the composite and then the threaded shaft 19 is passed through the retaining ring 25 and the shim 27 and down through the hole 31 and screwed securely into the tooth. One now has an upstanding spherical member firmly attached to the broken off stub of the tooth which forms a firm anchor for the attachment of a prosthetic tooth.

Figure 3:
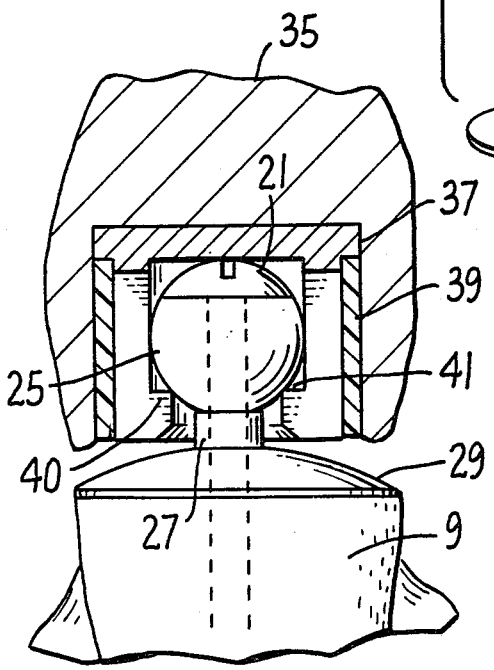
FIG. 3 is a section showing how the device of FIG. 1 is used to anchor a crown.

One method of applying the prosthetic tooth is shown in FIG. 3. Here an artificial tooth 35 has a partially hollowed out interior with the cup-like member 37 and a collar 39 with inturned lip 40 formed within the hollow tooth. The hollow interior is filled with a dental cement 41 after the attaching device is snapped down over the ball formed by parts 21 and 25. When the cement hardens, the operation is complete.

Figure 2:
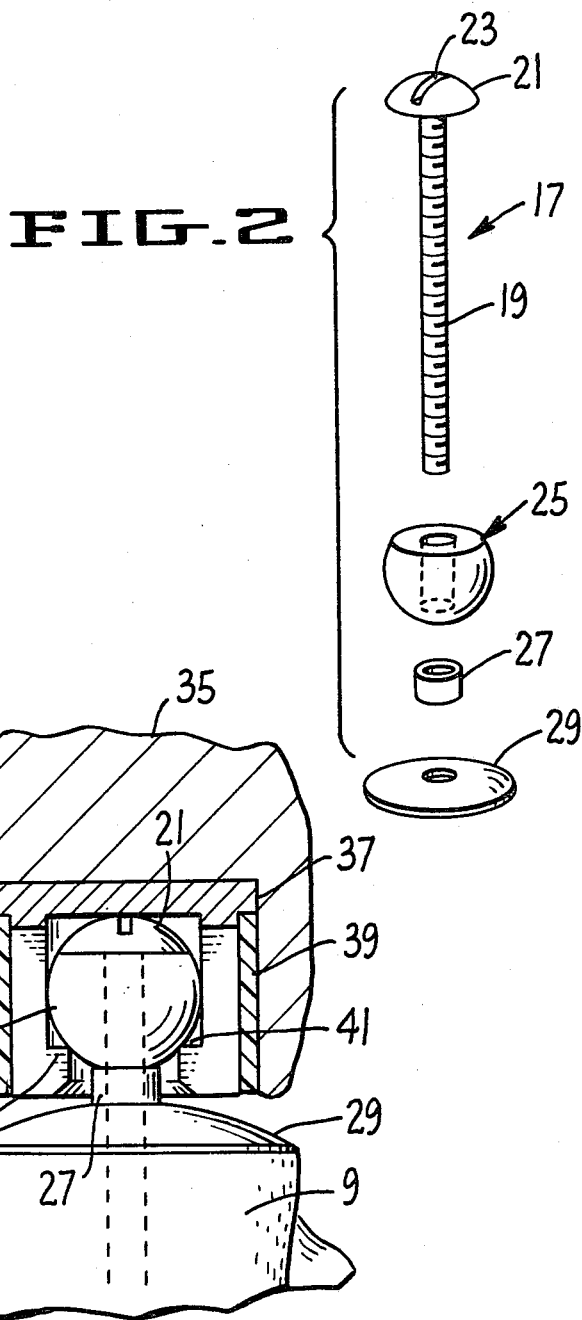
FIG. 2 is an exploded view of the device shown in FIG. 1.
Figure 4:
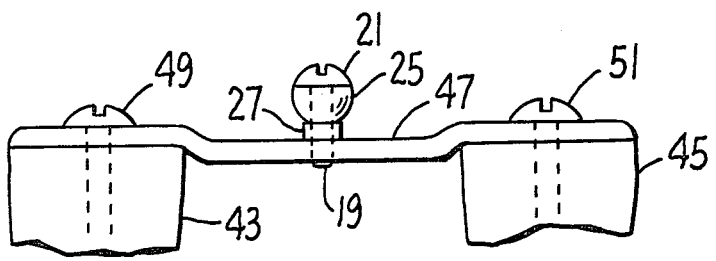
FIG. 4 shows another application of the denture retaining device wherein it is shown bridging two broken teeth.

In FIG. 4 another application of the device of the present invention is shown. Here is it desired to support a bridge or similar prosthesis between two broken off teeth designated 43 and 45. A bar 47 is provided which stretches between the two stumps of teeth and this is bolted to the teeth by means of the bolts 49 and 51 which can be of the structure cited above as number 17. At the center of the bridging member 47 a bolt, as shown in FIG. 2, is installed except that the coping dish 29 is omitted. Thus the bolt has a head 21, a shaft 19, a retaining ring 25 and a shim 27. This provides a sturdy structure and a bridge or other prosthesis may be applied to the upstanding ball as a detachable prosthesis.

Figure 5:
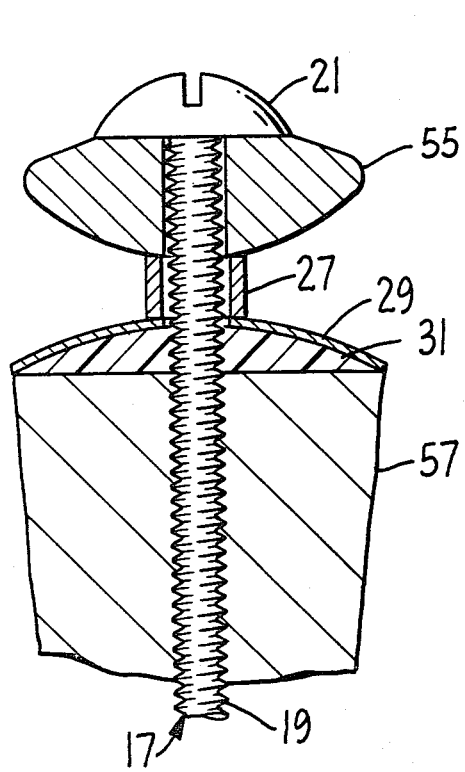
FIG. 5 is a section similar to FIG. 1 showing another embodiment of the invention.
Figure 6:
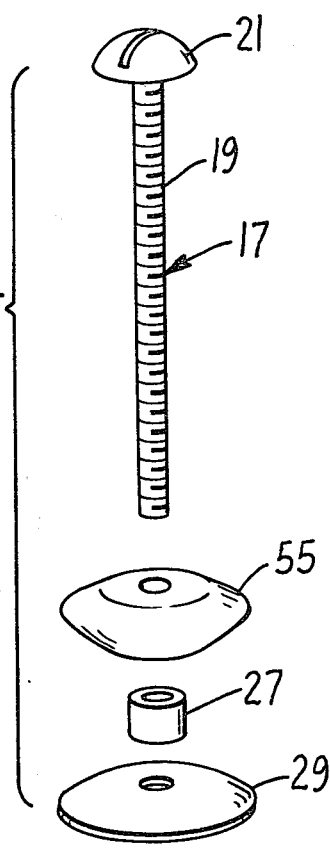
FIG. 6 is an exploded view of the device shown in FIG. 5.
Figure 7:
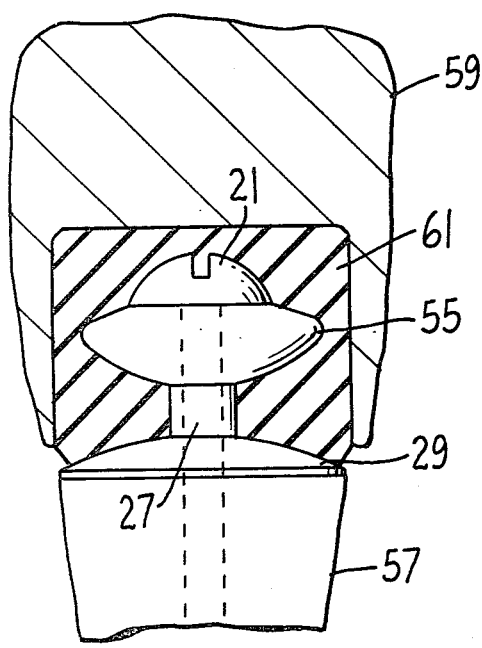
FIG. 7 is a section through a tooth root showing how the device of FIG. 5 is employed to hold an aritificial tooth.

In FIGS. 5-7 a similar embodiment of the invention is shown showing the same bolt 17 with threaded shaft 19, head 21, shim 27 and coping dish 29. However, in this instance, instead of the retaining ring 25 which is in the shape of a spherical segment, a metal retaining ring 55 is employed which is in the shape of an oblate spheroid. In this application the device is employed substantially like that of FIG. 1 so that the tooth stump 57 is drilled and tapped as before, coated with the composite 31 and then the threaded shaft 19 is driven into the tooth 57 holding the retaining ring 55, shim 27 and coping dish 29 securely against the tooth. This device is employed exactly as previously described so that referring to FIG. 7 the broken tooth 57 is provided with the device of FIG. 5 and aritificial tooth 59 having a hollow interior is filled with an elastic material such as dental silicone rubber 61 and pressed down over the retainer. As soon as the elastic material 61 sets, the operation is complete.

Figure 8:
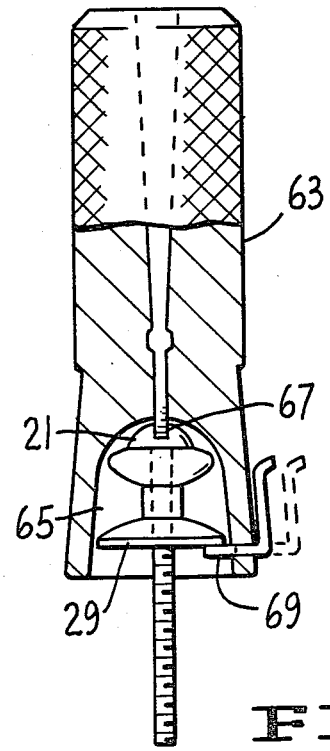
FIG. 8 is a section through a driver which can be advantageously employed in connection with the present invention.

The driver shown in FIG. 8 can advantageously be employed in carrying out the present invention. This consists of a handle 63 having a circular opening near the bottom 65 of a diameter which just clears the coping dish 29. Inside the hollow portion 65 is a screw driver bit 67 which protrudes into the cavity as shown. This device allows one to get a good grip on the bolt and drive it home without dropping any parts. To prevent this form happening, a sliding pin 69 is provided which protrudes into the cavity 65 and holds the parts in assembled relationship. The pin is retracted to the position shown in dash lines after the screw is started into the threaded hole.

Although certain embodiments of the invention have been brought out in the foregoing specification, it will be obvious to those skilled in the art that many variations can be made in the device and method of using the device without departing from the spirit of this invention.

I claim:

1. A device for holding a dental prosthesis such as a crown comprising in combination:
   a. a threaded shaft adapted to screw directly into a prepared threaded hole in a tooth,
   b. a head on said shaft, said head being a spherical segment of less than a hemisphere,
   c. a thick bulbous retention ring fitting over said shaft, said retention ring having a diameter larger than said head and having a top surface complimentary to the bottom surface of said head,
   d. a shim mounted on said shaft under said retention ring said shim having a smaller diameter than said head,
   e. a coping dish having a concave side and a convex side and having a diameter larger than said head mounted on said threaded shaft,
   f. said threaded shaft extending through said retension ring, shim, and coping dish whereby the concave side of said coping dish can lie on the surface of a prepared tooth with the threaded shaft extending into said tooth.

2. The device of claim 1 wherein said retention ring is complementary to said head whereby said head and said retention ring fit together to form a complete sphere.

3. The device of claim 1 wherein said retention ring is an oblate spheroid of a metal material.

4. The device of claim 3 wherein said retention ring is made of a silicone rubber.

5. The method of fitting a prosthetic tooth on a tooth root comprising:
   a. drilling and threading a hole in said tooth root,
   b. applying a dental composite over the exposed surface of said tooth,
   c. placing a coping dish over said composite with the concave side of said dish toward the dental composite, said coping dish having a central opening,
   d. inserting the threaded member of claim 1 through said hole of screwing the member into said tooth root,
   e. applying a dental cement around the thus located retention ring, shim and coping dish and,
   f. fitting a crown over said tooth root with said dental elastic material filling the hollow interior of said crown.

* * * * *